United States Patent [19]
Greene

[11] 3,999,177
[45] Dec. 21, 1976

[54] VEHICLE OPERATOR ALERT SENSOR AND ALARM

[76] Inventor: Harold L. Greene, 44 Rock Ridge Road, Dover, N.J. 07801

[22] Filed: Apr. 18, 1975

[21] Appl. No.: 569,488

Related U.S. Application Data

[63] Continuation-in-part of Ser. No. 401,357, Sept. 27, 1973, abandoned, which is a continuation-in-part of Ser. No. 323,831, Jan. 15, 1973, abandoned.

[52] U.S. Cl. .......................... 340/279; 179/182 R; 200/DIG. 2
[51] Int. Cl.² ........................................ G08B 21/00
[58] Field of Search .......... 340/279, 283; 128/151; 179/182 R, 107 H; 200/DIG. 2, 220

[56] References Cited
UNITED STATES PATENTS

| 2,910,679 | 10/1959 | Baldwin | 340/279 |
| 3,208,062 | 9/1965 | Gregory | 340/279 |

FOREIGN PATENTS OR APPLICATIONS

| 1,297,003 | 6/1969 | Germany | 340/279 |

OTHER PUBLICATIONS

"Transistorized Driver Alarm," Popular Electronics, vol. 12, No. 3, Mar. 1960, pp. 98,99.

*Primary Examiner*—John W. Caldwell
*Assistant Examiner*—William M. Wannisky
*Attorney, Agent, or Firm*—LeBlanc & Shur

[57] ABSTRACT

Disclosed is apparatus for keeping a vehicle operator awake by means of an audible alarm or signal responsive to a nodding or tilting forward movement of the head of the operator of the vehicle. The apparatus includes a switch mounted on a hat, ear hook or head band, worn by the vehicle operator and which switch is closed upon the tilting forward of the operator's head to complete an electrical circuit providing power from a battery to an alarm. The battery and alarm may be enclosed in a casing which may be clipped to the operator's wearing apparel, or mounted on the dash board of a vehicle and a flexible electrical line interconnects the hat, head band or ear hook and the casing or dash board to permit freedom of operator movement; also, an electrical connector may be provided on the flexible electrical line to permit the hat, head band or ear hook and casing or dashboard to be electrically and mechanically disconnected. A manually operable switch is provided to permit the alarm means to be selectively turned on or off.

9 Claims, 9 Drawing Figures

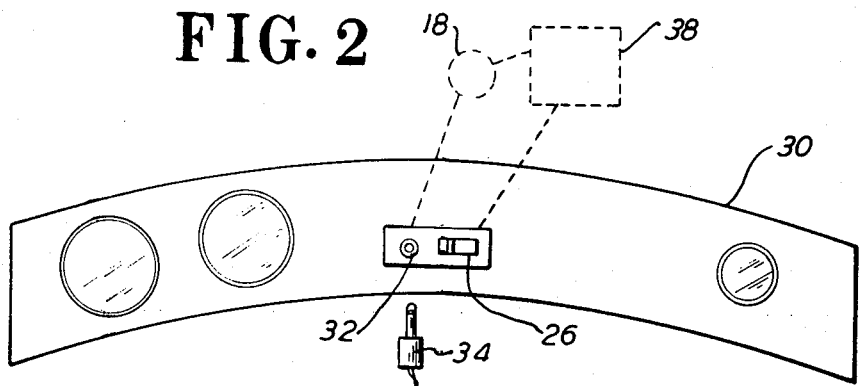
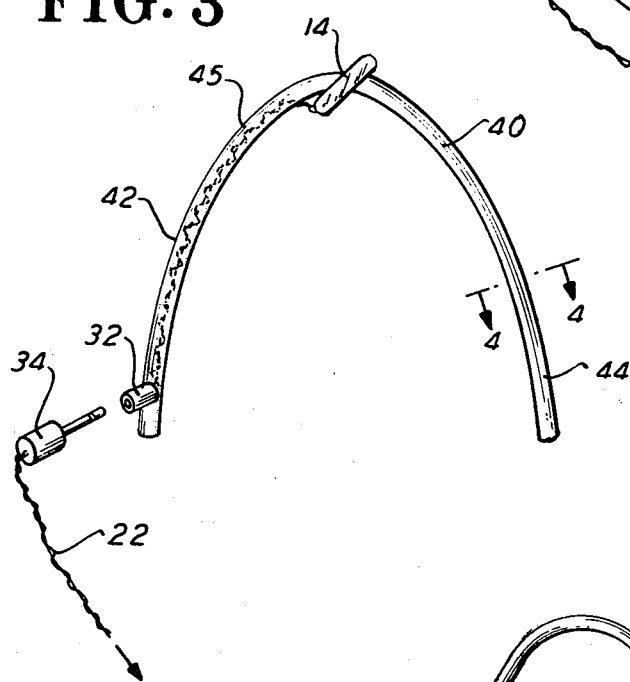
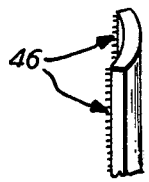
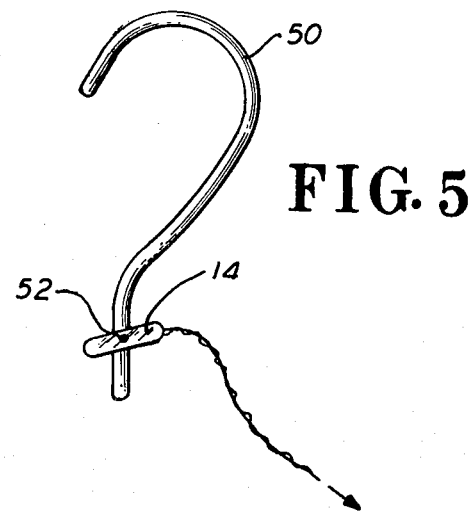

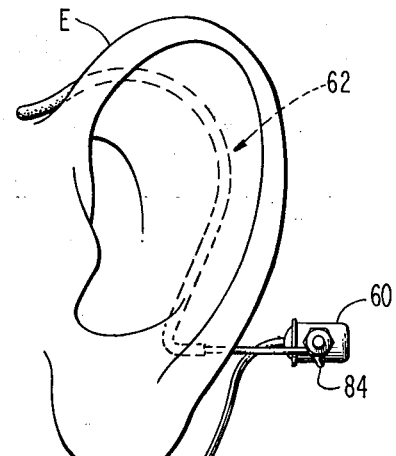
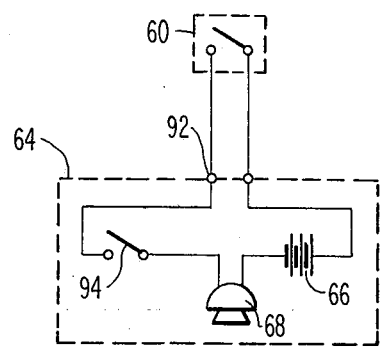
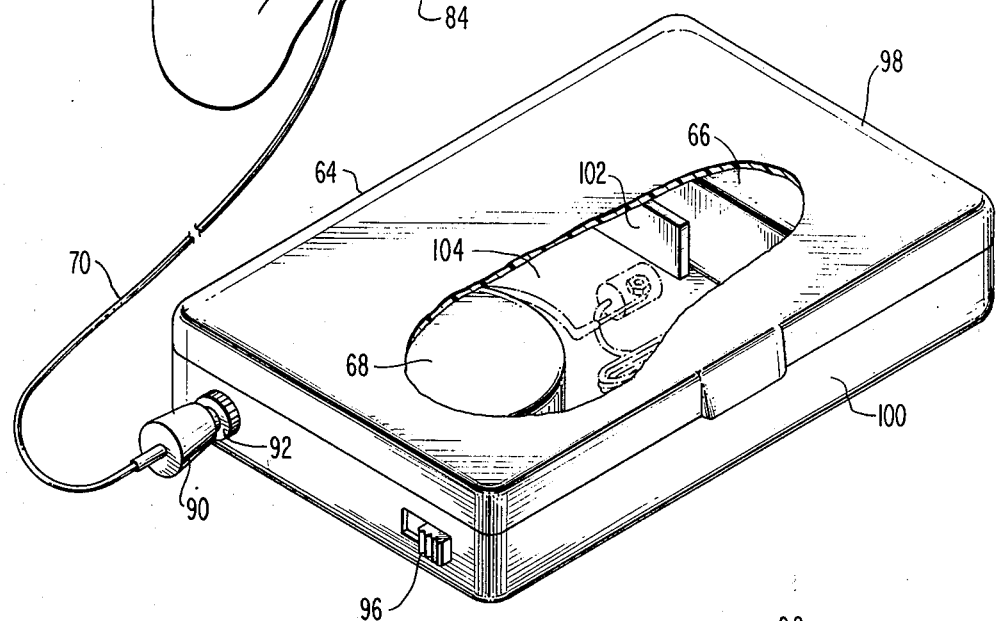
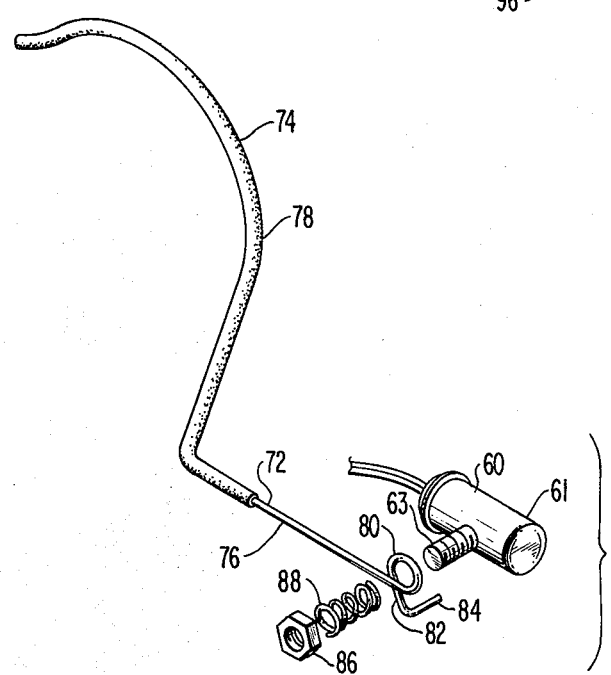
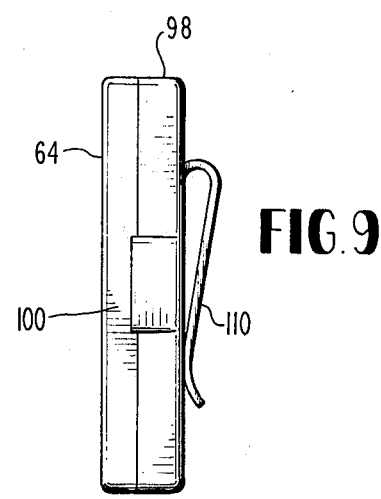
FIG.6
FIG.7
FIG.8
FIG.9

VEHICLE OPERATOR ALERT SENSOR AND ALARM

CROSS REFERNECE TO RELATED APPLICATION AND PATENTS

This application is a continuation-in-part of U.S. Patent Application Ser. No. 401,357 filed Sept. 27, 1973 which in turn is continuation-in-part of U.S. patent application Ser. No. 323,831 filed Jan. 15, 1973, both now abandoned. This application relates to the same general subject matter as applicants U.S. Pat. No. 3,076,186, issued Jan. 29, 1963.

BACKGROUND OF INVENTION

The present invention relates to an alarm apparatus for maintaining the operator of a motor vehicle awake and particularly relates to novel and improved alarm apparatus responsive to nodding or tilting forward movement of the head of the vehicle operator to provide an audible alarm signal which alerts the vehicle operator and prevents him from dozing or falling asleep.

The prior art is replete with numerous devices and apparatus for providing an audible alarm or signal to a vehicle operator to keep the operator awake and alert should the operator start to doze or fall asleep. However, such prior art devices and apparatus are typically prohibitively expensive and complex, and very often so cumbersome and/or restrictive of normal vehicle operator movement that they become offensive to the vehicle operator and the operator will not use them.

SUMMARY OF THE INVENTION

The present invention provides an alarm apparatus for maintaining a vehicle operator awake and alert which minimizes or eliminates the foregoing and other problems associated with prior alarm apparatus and provides a novel and improved alarm apparatus having various advantages in construction, mode of operation, use and result in comparison with such prior alarm apparatus. More particularly, the apparatus of the present invention includes a hat, head band or ear hook to be worn by the vehicle operator without discomfort or restriction of normal vehicle operator movement. A switch mounted on the hat, head band or ear hook worn by the operator is closed to complete an electrical circuit upon the head of the operator nodding or tilting forward should the operator doze or fall asleep. Closure of the switch completes an electrical circuit and actuates an alarm which provides an audible signal for awakening the vehicle operator. The hat, head band or ear hook and the alarm may be interconnected by a flexible electrical line further permitting unrestricted movement of the operator particularly with regard to normal vehicle operator movement or activity. A disconnector may be provided on the flexible electrical line for permitting the alarm and hat, head band or ear hook to be mechanically and electrically disconnected thereby enabling the operator to conveniently leave the vehicle. Also, a manually operated switch may be provided to permit the alarm apparatus to be selectively turned on and off.

In a preferred form of the present apparatus, the alarm apparatus comprises a power source, an alarm, a switch electrically coupled to the power source such that the alarm is actuated in response to closing the switch, and an ear hook having an arcuate portion for engaging over and behind the operator's ear and a portion cantilevered from the lower end of the arcuate portion. The switch is carried adjacent the distal end of the cantilevered portion and is adapted for acting in response to movement of the individual's head from a generally upright position to a predetermined forward inclination. The switch is pivotally mounted to the ear hook and can be infinitely angularly adjusted relative to the horizontal with a predetermined range and retained in such adjustment whereby the degree of inclination of the operator's head necessary to activate the alarm can be preselected. Also, the range of pivotal movement of the switch relative to the ear hook is limited by an abutment whereby the switch is maintained at all times in an angular position in which the alarm can be actuated when the ear hook is worn.

Accordingly, it is a primary object of the present invention to provide a novel and improved apparatus for sensing the alertness of an individual and providing an alarm in the event the individual becomes drowsy.

It is another object of the present invention to provide a novel and improved apparatus responsive to movement of an individual's head from a generally upright position to a forwardly inclined position to sound an alarm.

It is still another object of the present invention to provide a novel and improved apparatus for maintaining a vehicle operator awake by means of an audible alarm responsive to a nodding or tilting forward movement of the vehicle operator's head.

It is a further object of the present invention to provide a novel and improved apparatus for maintaining the operator of a vehicle alert and awake and which apparatus is characterized by an ear hook worn by the operator and mounting a normally open switch whereby the switch closes and completes an electrical circuit to sound an alarm in response to a nodding forwardly or forward inclination of the vehicle operator's head.

It is a still further object of the present invention to provide a novel and improved alarm apparatus having the foregoing characteristics and wherein the switch constitutes a mercury switch angularly adjustable relative to the horizontal whereby the angle of inclination of the individual's head necessary to close the switch and actuate the alarm can be preselected.

It is a still further object of the present invention to provide a novel and improved alarm apparatus having the foregoing characteristics, and wherein the switch is infinitely angularly adjustable within a predetermined range determined by an abutment carried by the ear hook and which abutment limits the angular movement of the switch in opposite directions.

It is a related object of the present invention to provide a novel and improved alarm apparatus having the foregoing characteristics and wherein such apparatus is simple and economical to manufacture, is reliable and repeatable, and is readily, easily and comfortably worn by the vehicle operator.

DESCRIPTION OF THE DRAWINGS

These and further objects and advantages of the present invention will become more apparent by reference to the following specification, appended claims and drawings wherein:

FIG. 2 is a diagrammatic illustration of a further embodiment of the present invention wherein the alarm means and other structure are mounted on the vehicle;

FIG. 3 is a further embodiment of the present invention wherein the alarm actuating switch forms a part of a generally inverted U-shaped head band to be worn by a vehicle operator;

FIG. 4 is a partial sectional view taken substantially along line 4—4 in FIG. 3 in the direction of the arrows and showing in detail the fine teeth which may be provided on the underside of the legs of the inverted U-shaped head band;

FIG. 5 is a further embodiment of the present invention wherein the alarm actuating switch is mounted on an ear hook to be worn by a vehicle operator;

FIG. 6 is a schematic illustration of a preferred embodiment of the present invention in the form of an ear hook shown applied to an individual's ear and mounting the switch which is attached by an electrical line to a case illustrated in perspective;

FIG. 7 is a schematic diagram of an electrical circuit for use with the embodiment of the present invention illustrated in FIG. 6;

FIG. 8 is a perspective view of the ear hook and switch with the connecting parts between the ear hook and switch illustrated in exploded juxtaposition; and FIG. 9 is a side elevational view of another form of the case for use with the embodiment hereof illustrated in FIG. 6.

DETAILED DESCRIPTION OF THE INVENTION

Figure 1:
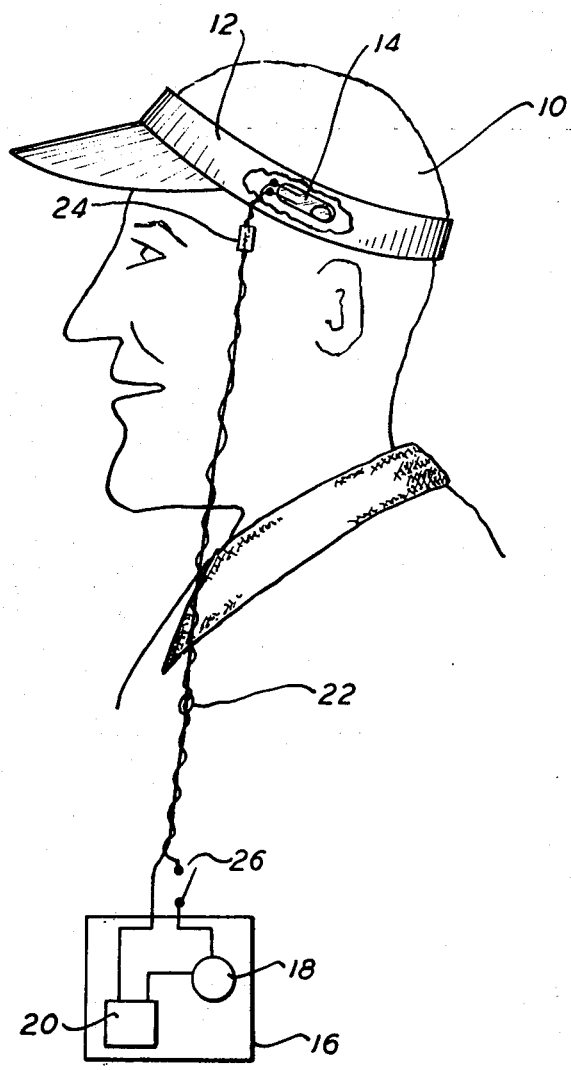
FIG. 1 is a diagrammatic illustration of a first embodiment of the present invention wherein the alarm actuating switch forms a part of a hat to be worn by a vehicle operator.

Referring now to FIG. 1, there is shown a typical vehicle operator 10 who is shown equipped with a first embodiment of the alarm apparatus of the present invention and which apparatus is shown in the operating position on the vehicle operator.

The apparatus includes a hat 12 to be worn by the vehicle operator and which hat may be, for example, a light visored cap as shown or other hand gear typically worn by a vehicle operator.

Mounted in the hat 12, such as being sewn in or otherwise attached to the material of the hat, is a switch 14, e.g. a mercury tube switch, including a pair of normally open contacts and a globule of mercury as shown.

Suitably mounted inside of a casing 16, which casing may be made of a suitable light material such as plastic, are alarm means 18 for providing an audible alarm or signal upon the operation thereof to keep the vehicle driver awake and power means 20 for operating the alarm means 18. The alarm means 18 may be, for example, a suitable battery operated buzzer, and, the power means 20 may be, for example, a suitable replaceable battery. The casing 16 may be provided with suitable clip means, such as a spring for securing the casing to the wearing apparel of the vehicle operator, e.g. the operator's shirt pocket.

Interconnecting the alarm means 18 and power means 20 is a suitable flexible electrical cord 22 for electrically interconnecting the mercury tube switch 14 and the alarm means 18 and power means 20.

Connected to the flexible electric cord 22 are disconnecting means 24 which may be manually operated to mechanically and electrically disconnect the hat 12 from the alarm means 18 and power means 20. Such disconnecting means may be comprised of suitable complementary male and female electrical connectors.

A manually operable switch 26 is provided for manual operation by the operator to electrically disconnect the alarm means 18 from the power means 20 thereby permitting the apparatus to be selectively turned on and off by the operator 10.

In operation, the hat 12 is first placed on the operator's head in an upright position, substantially as shown in the drawing, and with the operator's head in the normal upright position it will occupy under normal vehicle operating positions. The switch 26 is then placed in the on position to activate the alarm apparatus. Should the alarm apparatus 18 be activated by the switch means 14 to render an audible alarm or signal the hat can be adjusted by raising the visor upwardly or moving the back of the hat downwardly until the alarm means 18 is rendered inoperable with the operator's head in his normal vehicle operating position. Conversely, should the audible alarm means 18 remain deactivated when the operator's head is nodded forwardly to the position it would occupy should the operator begin to doze or fall asleep, the visor of the hat can be pulled downwardly in front or the back of the hat can be raised upwardly.

Referring now to FIG. 2 there is shown a further embodiment of the present invention wherein the alarm means 18, instead of being mounted in the casing 16 of FIG. 1, is mounted on the vehicle operated by the operator 10. In this embodiment of the present invention, the disconnecting means 24 of FIG. 1 includes a female connector 32 and a male connector 34 connected to the flexible electrical cord 22. The female connector 32 and the manually operable switch 26 are mounted on the dash board 30 of the vehicle operated by the operator. Also, in this embodiment, instead of utilizing power means 20 mounted in the casing 16 of FIG. 1, the apparatus for keeping a vehicle operator awake is powered by power means which may be the battery 38 of the vehicle operated by the vehicle operator. To activate or enable the apparatus embodiment of FIG. 2, the operator upon entering the vehicle inserts the male connector 34 into the female connector 32 and adjusts the hat 12 in the manner described above with regard to the embodiment of FIG. 1. It will also be recognized by those skilled in the driver alert art that the embodiment of FIG. 2 also provides a vehicle operator 10 with the freedom of movement described above.

Referring now to FIG. 3, there is shown a further embodiment of the present invention wherein the headgear on which the alarm actuating switch is mounted is an inverted generally U-shaped head band 40 including legs 42 and 44. In this embodiment of the invention, the switch means 14 (mercury tube switch) is suitably mounted on the head band 40, as shown, as is the female connector 32; the switch means 14 being electrically interconnected with the female connector 32 by a wire 45 shown in dashed line and suitably secured to the underside of the leg 42 of the head band 40. In the embodiment of FIG. 3, the alarm means 18 and power means 20 may either be mounted in the casing 16 of FIG. 1 or may be mounted in the vehicle operated by the vehicle operator as illustrated in FIG. 2. To enable or activate the apparatus for keeping a vehicle operator awake in the embodiment of FIG. 3, the male connector 34 is inserted into the female connector 32 and the head band 40 is adjusted in the same manner as described above with regard to the adjustment of the hat 12 of FIG. 1. Referring to FIG. 4, it will be further understood by those skilled in the art that the underside of the legs 42 and 44 of the head band 40 may be provided along their outer edges with fine teeth 46 for assisting in maintaining the head band 40 on the head of the vehicle operator.

Referring now to FIG. 5, there is shown a further embodiment of the present invention wherein the headgear to be worn by the vehicle operator constitutes an ear hook 50, which may be, for example, a plastic covered wire suitably shaped to be fitted around an ear of the vehicle operator. In the embodiment of FIG. 5, the switch means may be, for example, a mercury tube switch 14 as shown in FIG. 1, which may be suitably secured to the ear hook 50 by a screw or rivet which mounts the switch means 14 pivotally on the ear hook 50. By being mounted pivotally on the ear hook 50, the switch means 14 may be manually pivoted or tilted so as to adjust the apparatus to assure that upon the tilting or nodding forward of the head of the vehicle operator the apparatus will be activated at the proper time, and conversely, may be pivoted or tilted in the opposite direction to assure that the apparatus is not operated to sound the alarm means 18 upon normal head movement of the vehicle operator. As with regard to the embodiment of FIG. 3, the alarm means 18 and power means 20 may be either mounted in a casing 16 worn by the vehicle operator as shown in FIG. 1, or, as illustrated in FIG. 2, the alarm means may be mounted on the dashboard of the vehicle operated by the vehicle operator and the apparatus may be powered by the vehicle battery.

Referring now to FIGS. 6–9, there is illustrated a further embodiment of the driver alert sensor and alarm device hereof. Particularly, the apparatus includes a switch 60 mounted on a support, i.e. an ear hook generally designated 62, a case or container 64 carrying a power source, i.e. a battery 66 and an alarm 68, together with a flexible electrical line 70 electrically coupling switch 60 to the power source and alarm in a manner to be described. Referring now particularly to FIGS. 6 and 8, the ear hook 62 comprises an element for supporting switch 60 such that the weight of the switch and the weight and/or pull of the flexible electrical line 70 acts on the ear hook whereby the force exerted on the individual's ear by the ear hook 62 is transferred to the individual's ear substantially along the lower back of the ear. The lower back of an individual's ear is, of course, sensitive to pressures or forces acting thereon than, for example, the top of the ear. To accomplish this, ear hook 62 is comprised of an elongated spring steel wire 72 having a portion 74 shaped in the form of a hook to engage over and behind an individual's ear designated E (FIG. 6) and another portion 76 cantilevered from the lower end of the arcuate portion 74 to extend in a direction away from arcuate portion 74. The wire 72, at least for that portion thereof engaging over and behind the ear E, is preferably coated with a plastic material 78 to render the ear hook 62 more comfortable when worn.

The cantilevered portion 76 terminates in a wire loop 80 (FIG. 8) which lies substantially in the plane of the ear hook 62. The distal end 82 of the wire 72 extends downwardly a short distance at which point it forms a projection 84 which extends generally normal to the plane containing ear hook 62 and loop 80 for reasons described in detail hereinafter.

Switch 60 is preferably a mercury switch housed in a substantially cylindrical metal container 61. Container 61 has a threaded shaft 63 suitably secured thereto and which shaft 63 projects to one side of container 61 normal to its long axis. Switch 60 is carried at the end of the cantilevered portion 76 of ear hook 62 at a location remote from the arcuate hook portion 74. Particularly, the shaft 63 which projects from switch container 61 is inserted through the wire loop 80 and switch 60 is secured thereto by means of a nut 86 and a coil spring 88 disposed between nut 86 and the wire loop 80. Consequently, it will be appreciated that switch 60 is mounted adjacent the distal end of the cantilevered portion 72 of ear hook 62 for pivotal movement about a substantially horizontal axis (coincident with the axis of shaft 63) when the ear hook 62 is applied to the ear of an individual as illustrated in FIG. 6. Also, coil spring 88 biases the metal container 61 housing switch 60 into engagement with the wire loop 80 whereby the switch substantially frictionally engages loop 80 in selected adjusted angular position about the axis of shaft 63. As discussed in detail hereinafter, the projection 84 extends below the switch housing 61 in substantial vertical alignment with the axis of rotation of switch housing 61 about shaft 63 when the device is worn as illustrated in FIG. 6. Projection 84 thus serves to limit the extent to which switch 60 is pivotable about shaft 63 within a predetermined angular range.

The flexible electrical line 70 is connected to contacts, not shown, at the forward end of mercury switch 60. The opposite end of flexible electrical line 70 terminates in a plug 90 receivable in a jack 92 located at one end of case 64. Referring to FIG. 7, it will be seen that the power source 66, i.e. a battery, and alarm 68, i.e. a buzzer, are connected in series with mercury switch 60 through jack 92 and with an on-off switch 94. Switch 94 includes a switch actuating element 96 (FIG. 6) carried by casing 64 at one end thereof and for external actuation.

Case 64 comprises a box having a lid 98 suitably hinged to a box base 100 along an edge thereof whereby access to the contents of case 64 can be obtained by pivoting lid 98 to a case open position from its closed position illustrated in FIG. 6. Interiorly of case 64, ribs 102 are provided for securing the battery 66 within the case. Also, ribs, not shown, forming a part of the base 100 of case 64 are also utilized to secure the alarm buzzer 68 within the case 64. Between the battery 66 and alarm 68, a cavity 104 is provided in the base of the case whereby the plug 90 and flexible electrical line 70 may be coiled and disposed within such cavity in the case with the ear hook 62 extending about the circular alarm buzzer 68. Accordingly, when the device hereof is not in use, it can be compactly stored in its case 64. In FIG. 9, the case 64 is illustrated with a spring clip 110 secured thereto. In this manner, case 64 can be affixed to the pocket or lapel of an individual utilizing the device.

To utilize the device, an individual opens the case 64 and removes the ear hook 62, electrical line 70 and plug 90. The plug 90 is then inserted into the female jack 92 and the ear hook is applied over the ear in such a manner that the switch 60 is carried at the distal end of the cantilevered portion 76 behind the ear substantially as illustrated in FIG. 6. Switch 94 is closed or turned to the "on" position by displacing switch actuating element 96 thereby completing the electrical circuit illustrated in FIG. 7 and enabling actuation of alarm 68 when mercury switch 60 is closed.

Assuming the individual's head is maintained in a substantially upright position or inclination, the degree of inclination of such individual's head necessary to actuate the alarm can be adjusted infinitely within a predetermined range simply by rotating the switch housing 61 and shaft 63 relative to the cantilevered portion 76 of the ear hook 62 to the desired angular position relative to the horizontal. For example, if the individual wishes actuation of alarm 68 in response to only a slight nodding or tilting forward of his head, the switch 60 is pivoted to a position wherein its axis forms a very small acute angle with the cantilevered portion 76 of the ear hook and wherein switch housing 61 is only slightly inclined to the horizontal with the mercury switch contacts, not shown, lying at the upper end of the inclined housing 61. Consequently, when the individual's head is slightly inclined forwardly the mercury switch contacts will close causing actuation of alarm 68. Should the individual desire actuation of the alarm only when his head has obtained a substantial degree of inclination in a forward direction, for example when the individual's chin lies closely adjacent his chest, switch 60 is pivoted such that the long axis of switch housing 61 forms a substantial acute angle with the cantilevered portion 76 with the mercury switch contacts, not shown, lying at the upper end of inclined housing 61. Thus, actuation of the alarm is caused only when the switch 60 is brought into a substantial horizontal position when the individual's head is substantially inclined forwardly with his chin adjacent his chest. Obviously, the angle of inclination of switch housing 61 may be adjusted infinitely within such aforedescribed range of extreme positions and, it will be appreciated that the spring biased frictional engagement of housing 61 and wire loop 80 serves to maintain the switch in the selected adjusted positions.

The projection 84 which extends below the switch housing 62 limits the range of pivotal movement through which switch housing 61 may rotate. For example, as illustrated in FIG. 6, clockwise or counterclockwise rotation of housing 61 causes it to engage wire projection 84, for example after 30°-35° rotation relative to the horizontal whereby wire projection 84 limits the range of angular movement of switch housing 61. This is important particularly when the device is removed from the individual's ear and then later replaced on his ear. In the absence of projection 84, the switch 60 might assume other angular orientation when removed and which angular positions might be insufficient to actuate the alarm. If the switch becomes out of adjustment, the individual will immediately become aware of this simply by nodding his head forwardly whereby the angle of inclination at which the alarm will actuate can be readily determined. If it is actuated at an undesirable angle of inclination, the individual can readily readjust the angular position of the switch whereby the alarm can again be activated at the desired inclination of the individual's head.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. Alarm apparatus comprising a power source, an alarm, a switch, means electrically coupling said source, said alarm and said switch for actuating said alarm in response to actuation of said switch, means for supporting said switch from the ear of an individual for movement with the individual's head including an ear engaging element formed of a resilient material and having a portion arcuately shaped to engage over and behind an individual's ear, said arcuately shaped portion lying in a plane which is substantially vertical when said element is mounted on the ear of an individual whose head is upright, said element also having an elongated switch support portion cantilevered from adjacent the lower end of said arcuate portion so as to extend substantially normal to the end of that portion of the ear engaging element which engages behind the ear, and means for mounting said switch on said cantilevered support portion adjacent the end thereof remote from said arcuate portion, said electrical coupling means including a flexible wire extending from said switch, said cantilevered support portion extending substantially in the plane of said arcuate portion and substantially in a horizontal direction when the individual's head is in an uprigth position whereby the weight of said switch and pull of said wire acting on the distal end of said cantilevered switch support portion acts on the ear engaging element such that the force transferred to the individual's ear acts substantially along the lower back of the ear generally into the back of the ear in the same direction as the face of the wearer, said means for supporting said switch from the ear of an individual and all appertenances thereto being so disposed as to provide unobstructed access to both the inner and outer cavities of the ear of said individual, said switch being position responsive so as to actuate said alarm when moved into a predetermined angular position relative to the horizontal and being so mounted that the angular position of said switch relative to said cantilevered support portion is adjustable whereby the degree of inclination of the individual's head necessary to actuate said alarm can be adjusted.

2. Apparatus according to claim 1 including means pivotally coupling said switch to said switch support portion for movement over a predetermined range of angular positions, and means for retaining said switch in selected adjusted angular positions within said predetermined range of angular positions.

3. Apparatus according to claim 2 wherein said means pivotally coupling said switch to said switch support portion includes a shaft projecting from said switch and being at least partially threaded, said switch support portion of said element including an opening for receiving said shaft, a nut threaded on said shaft, and a spring about said shaft between said nut and the margins of the switch support portion about said opening for biasing said switch against said switch support portion to increase frictional resistance to pivotal movement of said switch.

4. Apparatus according to claim 3 including means for limiting the range of pivotal movement of said switch at least in one angular direction relative to said switch support portion.

5. Apparatus according to claim 4 wherein said limiting means includes a projection extending from said distal end of said switch support portion substantially normal thereto to one side of the pivotal axis of said switch substantially parallel thereto into the path of pivotal movement of said switch to form an abutment precluding such pivotal movement in said one angular direction.

6. Apparatus according to claim 5 wherein said opening is formed by a loop in said switch support portion with said shaft on said switch being secured in said opening formed by said loop by means of said nut and spring.

7. Apparatus according to claim 6 wherein said ear engaging element is formed of spring steel wire coated with a plastic material over at least a portion thereof.

8. Apparatus according to claim 1 wherein said ear engaging element is formed of spring steel wire coated with a plastic material over at least a portion thereof.

9. Apparatus according to claim 1 including a case for housing said alarm and said power source, said flexible wire extending from said switch being connected to said container, an on-off carried by said case for disabling said alarm when said on-off switch is off and enabling actuation of said alarm in response to actuation of the first mentioned switch when said on-off switch is on.

* * * * *

UNITED STATES PATENT AND TRADEMARK OFFICE
CERTIFICATE OF CORRECTION

PATENT NO. : 3,999,177
DATED : December 21, 1976
INVENTOR(S) : Harold L. Greene

It is certified that error appears in the above-identified patent and that said Letters Patent are hereby corrected as shown below:

Column 10, line 4, after "on-off", insert --switch--

Signed and Sealed this

Tenth Day of May 1977

[SEAL]

Attest:

RUTH C. MASON
*Attesting Officer*

C. MARSHALL DANN
*Commissioner of Patents and Trademarks*